United States Patent [19]

Lewin

[11] 4,225,316
[45] Sep. 30, 1980

[54] CHEMICAL AGENT DETECTION METHOD AND APPARATUS

[75] Inventor: Seymour Z. Lewin, Bayside, N.Y.

[73] Assignee: The United States of America as represented by the Secretary of the Navy, Washington, D.C.

[21] Appl. No.: 157,299

[22] Filed: Nov. 28, 1961

[51] Int. Cl.³ .................. G01N 33/00; G01T 1/00; G01T 3/06

[52] U.S. Cl. .................. 23/230.3; 23/230.6; 23/232 R; 73/23; 250/252; 250/303

[58] Field of Search .......... 23/230, 232, 254, 232 R, 23/230.3, 230.6; 250/43.5, 47, 252, 303; 73/23

[56] References Cited

U.S. PATENT DOCUMENTS

| | | | |
|---|---|---|---|
| 2,741,544 | 4/1956 | Chaikin et a. | 250/252 X |
| 2,926,072 | 2/1960 | Kramer et al. | 23/232 R |
| 2,968,722 | 1/1961 | Chleck et al. | 23/230.3 |
| 3,025,141 | 3/1962 | Van der Smissen | 23/232 R |
| 3,366,574 | 1/1968 | Chleck | 23/232 R X |
| 3,451,901 | 6/1969 | Seiger et al. | 23/232 R |
| 3,660,036 | 5/1972 | Benson | 23/232 R X |
| 3,689,223 | 9/1972 | Poziomek et al. | 23/232 R |

*Primary Examiner*—Richard E. Schafer
*Attorney, Agent, or Firm*—R. S. Sciascia; Sol Sheinbein

EXEMPLARY CLAIM

1. The method of detecting predetermined organic halogen compounds in a gas comprising the steps of directing a sample of said gas into a reaction chamber containing immobilized therein a halogen compound in which the halogen constituent is radioactive, providing environmental conditions in said chamber to promote a chemical reaction whereby said radioactive constituent forms a mobile compound with a constituent of said organic halogen compound, and passing said sample including any of said mobile compound generated out of said reaction chamber and into the presence of a radiation detector.

11 Claims, 1 Drawing Figure

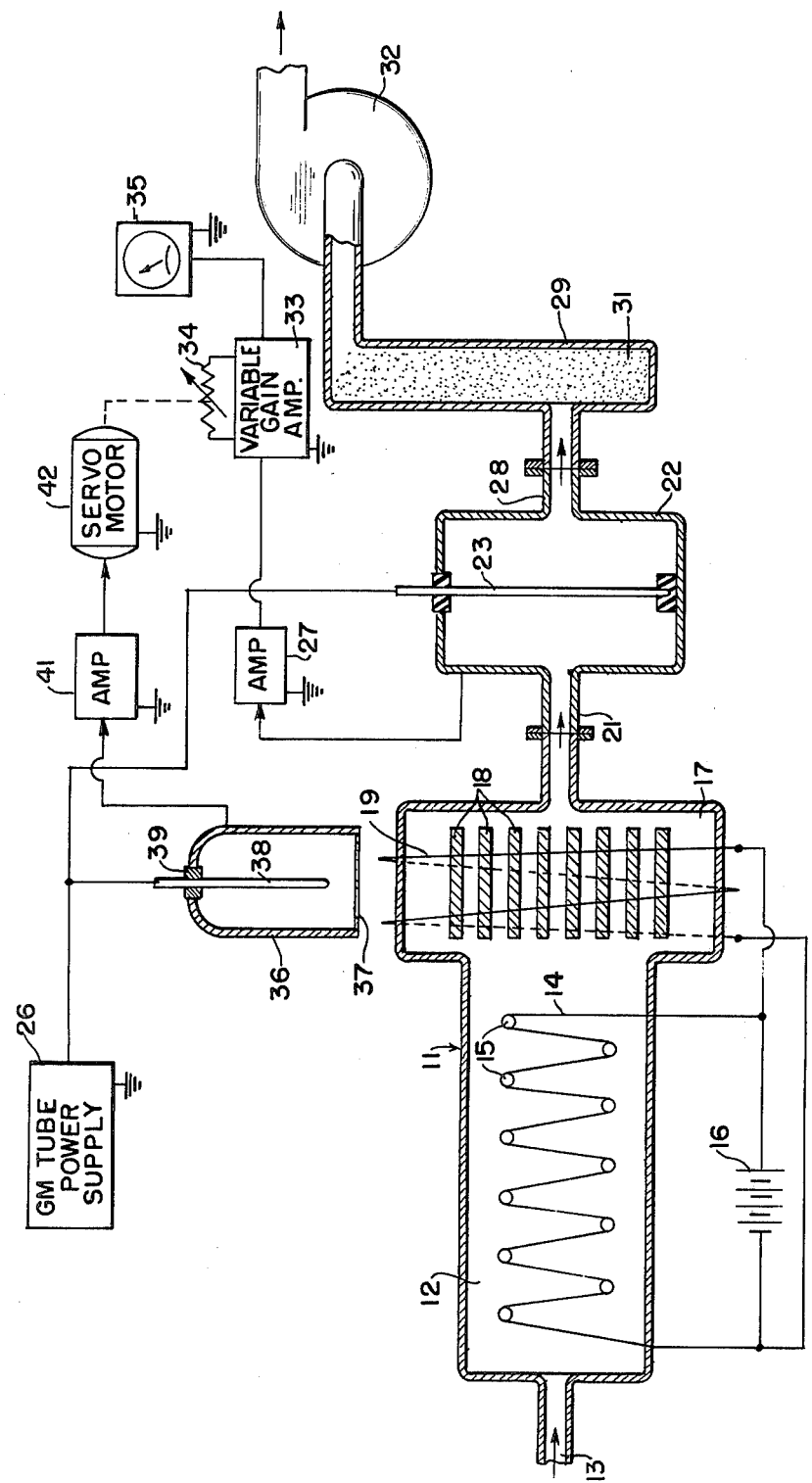

CHEMICAL AGENT DETECTION METHOD AND APPARATUS

This invention relates to an apparatus and method for detecting gases containing specific halogen containing compounds.

It is desirable for military and civilian defense purposes to have a reliable process and apparatus for detecting nerve gases which may be used in warfare. The chemistry of this kind of gas is well developed and the compounds which characterize these gases typically comprise halogen compounds (e.g. organic fluorophosphonates. A further characteristic is that they are not easily detected by ordinary means. It is vitally important for military and civilian defense purposes to detect them at an early stage and also to have a measure of their content in an area which is being subjected to de-contamination in order to detect accurately the point at which the area may safely be reoccupied. It is, accordingly an object of this invention to provide a method of detecting low concentrations of gases containing predetermined chemical agents, specifically, halogen-containing compounds in mixtures.

It is another object of the invention to provide a process utilizing the radioactivity of certain elements as an aid to detecting such predetermined chemical agents in gas mixtures.

It is another object of the invention to provide an apparatus suitable for the detection of low concentrations of gases containing predetermined chemical agents in any common kind of atmosphere notwithstanding the presence of the other constituents such as hydrocarbons or water vapor which are commonly encountered in the air. The term gas as used in this specification and the appended claims will be understood to include gases such as air containing other constituents as contaminants.

The operation of the invention in a typical embodiment contemplates the exposure of the gas sample to a radioactive halogen compound under environmental conditions such that radioactive halogen is released in a volatile state by virtue of oxidation-reduction reactions between the radioactive halogen compound and the halogencontaining compound forming a constituent of the chemical agent (in a typical case an organic fluorophosphonate). Since radioactivity of a gas mixture may be measured quite accurately and quantitatively by count of the number of radioactively disintegrating atoms, the characteristic of the method and apparatus is a degree of sensitivity far surpassing that of ordinary chemical analysis methods. It will be appreciated that the apparatus for carrying out the method typically comprises a reaction chamber with a gas sample input port, beds of radioactive material in the reaction chamber, heaters or other apparatus for creating the desired environmental conditions in the reaction chamber and an output port leading from the reaction chamber to a radiation measuring device.

Other objects and advantages of the invention will be apparent from reference to the following description in conjunction with the accompanying drawing which diagrammatically illustrates the combinations of elements comprising an illustrative form of apparatus and also will aid in the explanation of the several steps involved in the method of detection.

The method and apparatus according to the present invention can most readily be explained by reference to an illustrative embodiment of apparatus for carrying out the invention such as illustrated in the drawing. The illustrated apparatus is adapted for the detection of chemical agents containing an organic fluorophosphonate. Such chemical agents are utilized for other than military purposes (e.g. in insecticide sprays) as well as in nerve gases and it will thus be seen that the invention may be useful for other than military purposes.

The apparatus in the drawing comprises a reaction chamber 11 including a pyrolizing chamber 12. Hot-wire pyrolizing apparatus comprising a wire 14 of electrically conductive material (e.g. platinum) supported on insulating members 15 is arranged within the pyrolizing section 12. A suitable power supply 16 is provided for heating the pyrolizing wire 14.

The hot-wire pyrolizer section serves to pyrolytically decompose the fluorophosphonate compound into free radicals in order to promote a reaction between the fluorophosphonate constituents and the radio active compound at a later step of the process.

The second section of the reaction chamber 11 is the radioactive material section 17 which contains radioactive material 18 arranged in beds or otherwise disposed to come into contact with the gas sample.

The radioactive material section 18 is maintained at a suitable temperature, and environmental conditions are otherwise provided to facilitate selective reaction of the radioactive compound with the chemical agent.

In the apparatus illustrated a heater 19 is provided for maintaining the desired temperature in the radioactive material section 17. The heater 19 may be supplied from the same electrical power source 16 as was the hot wire pyrolizer. Obviously conventional apparatus for automatic control of temperature or other environmental conditions may be provided as necessary.

It should be pointed out that the pyrolizing section 12 may be unnecessary in certain forms of apparatus according to the invention due to the fact that the desired reaction may proceed with sufficient facility in the radioactive material section 17 without the necessity for previous pyrolization of the gas sample.

In the particular embodiment illustrated the radioactive material 18 comprises silver bromide where the bromine comprises a substantial quantity of radioactive bromine isotope No. 82.

The temperature of the chamber 17 in the particular example illustrated may be maintained at a temperature between 80° and 250° centigrade and the pressure therein may be between one-half and two atmospheres.

Under the foregoing conditions it has been demonstrated that a gas sample issuing from the reaction chamber 11 contains radioactivity in proportion to the amount of the fluorophosphonate compound that has entered the apparatus. At the same time no significant change in radioactivity is produced by commonly encountered atmospheric constituents such as oxygen, nitrogen, water vapor, hydrocarbons or the like. Obviously, radioactive contaminants in the atmosphere would produce an indication of radioactivity in the output from the reaction chamber. This may be desirable, but in the event that it was undesirable any radioactivity in the input sample could be measured and suitable compensation provided in the final radioactivity measurement.

While the operability of the apparatus is known primarily from experimental results, it is believed that the chemical reactions involved include one or more of the following reactions:

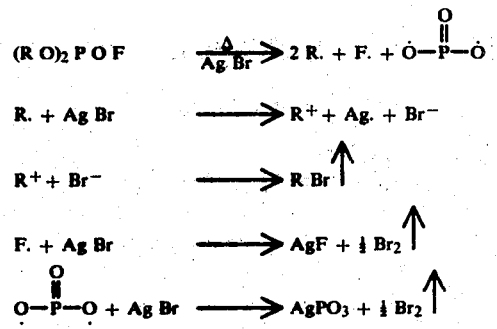

The radioactively tagged gas sample passes from chamber 11 through port 21 into a radioactivity detecting chamber 22.

The section 22 may comprise any suitable form of radioactivity detecting or measuring apparatus, and is illustrated as a Geiger-Mueller type radiation detector wherein a central anode is supplied with a DC electrical voltage with respect to the conductive outer wall of the chamber so that each radioactive emission results in ionization of the gas within the chamber and a pulse of current in the external circuit of the detector. The power supply for the radioactivity detector 22 is indicated at 26. An amplifier 27 may be provided in the circuit of the detector 22 to provide an amplified output proportional to the radioactivity detected.

The gas sample flows from the detection chamber 22 through an outlet channel 28 to a radioactivity trap 29 which contains a filter material 31 which reacts with the gas sample to remove the radioactive constituent. In the particular example illustrated the material 31 may be silver nitrate. After the radioactive constituent of the material has been trapped, the gas sample may be released to the atmosphere through pump 32 which serves to provide the pressure for drawing the gas sample through the apparatus. Obviously the pump 32 could be located at other places in the system or additional pumps could be provided if desired.

From the portion of the apparatus thus far explained, it will be apparent that the amount of radioactivity detected at the radiation detection chamber 22 will be a measure of the amount of the chemical agent in the sample drawn through the apparatus by pump 32. If the radioactivity of the material 18 remained substantially constant, the apparatus thus far described would be adequate for detection and measurement of predetermined chemical agents according to the present invention.

However, it is frequently desirable to use radioactive materials in the reaction chamber 11 which have half-lives of only a few days or weeks so that the variation in radioactivity of the material 18 would be fairly rapid and would effect the calibration of the apparatus. It will be noted for example that the half-life of bromine 82 is about 36 hours.

When a material having a relatively short half-life is utilized, further apparatus as illustrated in the drawing may be provided to continually and automatically correct for the decay in the radioactive material 18. The radioactive material 18 may be replaced periodically when it has decayed to the extent that the sensitivity of the apparatus is substantially reduced. For example, the $Ag B_r 82$ having a half-life of about a day and a half might be expected to be replaced on a weekly schedule, or more often if desired.

Referring again to the drawing a variable gain amplifier 33 is connected to the output of amplifier 27. The amplifier 33 is provided with a variable feedback resistor 34 to control the gain thereof.

The output of amplifier 33 is connected to a meter 35 or any other suitable indicator. It is contemplated that the pulse output from the detector 22 will be integrated over a short period of time (by virtue of the time constants of the electrical circuits) or otherwise modified by amplifiers 27 and 33 so that a substantially continuous output proportional to the rate of radiation count will be supplied to the variable gain amplifier 33. It is obvious, however, that digital or pulse techniques could also be utilized by slight modifications in the disclosed apparatus within the ability of those skilled in the art.

A second radiation detector 36 is provided and arranged to monitor the radioactivity of the radioactive material 18. The detector 36 may be provided with a window 37 for accepting radiation from the radioactive material 18. The detector 36 has an anode 38 mounted in insulated relationship by means of an insulating mounting 39 with respect to the cathode wall of the detector. The detector 36 may be powered from power supply 26.

Like radiation detector 22 it will be appreciated that any suitable form of radiation detector may be utilized in place of the Geiger-Mueller type detector 36 illustrated.

The output of detector 36 is supplied through an amplifier 41 to a servomotor 42 which is connected to adjust resistor 34 in proportion to the radiation received by detector 36. The response time of amplifier 41 (and servomotor 42) is sufficiently long to eliminate short term variations from detector 36. By this mechanism the gain of variable gain amplifier 33 is varied in inverse proportion to the radioactivity received by radiation detector 36. Thus the decay of the radioactive material 18, which would otherwise result in a proportionate reduction in the sensitivity of the apparatus is automatically compensated. Accordingly, a given quantity of predetermined chemical agent will produce substantially the same indication on meter 35 notwithstanding partial decay of the radioactive material 18. The variable gain amplifier and servomotor is given only by way of illustration and because it simplifies explanation. An all electronic equivalent compensation apparatus could be substituted in accordance with known techniques and would probably result in a more compact apparatus.

While the apparatus illustrated in the drawing has been explained in terms of detection of a particular chemical agent, namely one containing an organic fluorophosphonate, it should be appreciated that the apparatus can be adapted to the detection of various specific halogen containing compounds or classes of such compounds, and that further the apparatus can be adapted to detect still other classes of organic compounds which pyrolize at temperature below about 250° centigrade to yield free radical products.

As a further example of particular construction of the apparatus for detection of a different compound the apparatus previously described may be modified by utilizing as the radioactive material $AgI^{126}$. This modification of the apparatus renders it capable of detecting n-hexyl chloride with very good sensitivity.

Other radioactive isotopes of iodine may be utilized to form the radioactive material AgI. The following isotopes of iodine may be selected for particular applications in accordance with their respective half-lives as follows: $I^{124}$—4 days; $I^{125}$—56 days; $I^{126}$—13 days; and $I^{131}$—8 days.

In its broader aspect the invention contemplates the use of any radioactive silver halide as the radioactive material; for example, for detection of certain chemical agents it may be desired to utilize radioactive $AgCl^{36}$ as the radioactive material 18.

Fluorine is still another of the halogens which may be utilized as the radioactive material according to the present invention. Thus radioactive fluorine in one of the silver fluorides ($Ag_2F$, $AgF$, $AgF_2$) may provide the radioactive tracer element. Isotopes of fluorine have short half-lives but $F^{18}$ with a half-life of about two hours would be useful under special circumstances.

It will be noted that the apparatus described provides substantially an instantaneous indication of the presence of predetermined chemical agents (that is indication will generally be produced in a matter of seconds). It should be noted however, that this rapid indication may be sacrificed in preference to increased sensitivity if desired. Note for example that the radioactivity of the trap material 31 will represent the integrated value of radio active material produced and thus the integrated value of chemical agent detected. Thus a radiation detector placed in the trap 29 would be capable of detecting even smaller concentrations of the chemical agent. If it were desired to integrate the response to radioactivity over a shorter predetermined period of time the trap material such as silver nitrate could be impregnated in a web or tape and slowly moved passed the output channel 28 (or channel 21) so that the gas would pass through or impinge on the tape thereby trapping the radioactive element. The moving tape could then be monitored by a radiation detector at a point slightly displaced from the point of impingement of the gas.

In addition to those variations and modifications of the apparatus and method suggested herein it will be appreciated that numerous variations and modifications other than those suggested will be apparent to those of ordinary skill in the art.

Accordingly, it is desired that the scope of the invention not be limited to those specific embodiments shown or suggested but that the scope of the invention be limited solely by the appended claims.

What is claimed is:

1. The method of detecting predetermined organic halogen compounds in a gas comprising the steps of directing a sample of said gas into a reaction chamber containing immobilized therein a halogen compound in which the halogen constituent is radioactive, providing environmental conditions in said chamber to promote a chemical reaction whereby said radioactiive constituent forms a mobile compound with a constituent of said organic halogen compound and passing said sample including any of said mobile compound generated out of said reaction chamber and into the presence of a radiation detector.

2. The method of claim 1 wherein a non-halogen constituent of said halogen compound is silver.

3. The method of claim 1 wherein said halogen constituent is bromine.

4. The method of claim 1 wherein said halogen constituent is iodine.

5. The method of claim 1 wherein said halogen constituent is chlorine.

6. The method of claim 1 wherein said halogen constituent is fluorine.

7. The method of claim 1 further including the steps of measuring the radioactivity of said radioactive constituent with said radiation detector and providing an indication proportional to the radiation detected by said radiation detector and measuring the radioactivity of the immobilized radioactive halogen constituent in the reaction chamber with a second radiation detector and providing an indication inversely proportional to the radioactivity of said radioactive constituent.

8. The method of claim 1 further including the step of pyrolizing said organic halogen compound to promote the reaction between said organic halogen compound and said halogen compound.

9. The method as claimed in claim 1 wherein said reaction chamber is maintained at a temperature substantially above room temperature.

10. The method as claimed in claim 1 further including the step of passing said sample after the radiation therefrom has been detected into contact with a material having an affinity for said radioactive halogen element thereby trapping a substantial portion of said radioactive element to render said gaseous sample safe for release from the apparatus.

11. Apparatus for the detection of predetermined organic chemical agents in a gaseous atmosphere comprising a reaction chamber, means for transmitting a sample of gaseous atmosphere into said reaction chamber, a quantity of immobilized halogen compound in said reaction chamber, the halogen constituent of said compound being radioactive, means for controlling the temperature of said reaction chamber, means for measuring the radioactivity of the immobilized halogen compound in said reaction chamber, means for providing a signal inversely proportional to the radioactivity of the immobilized halogen compound an outlet from said reaction chamber, means disposed away from said reaction chamber for measuring the radioactivity of the gas emitted from said reaction chamber, and means for providing an indication proportional to the radioactivity of the gas emitted from said chamber.

* * * * *